United States Patent
Oh

(10) Patent No.: US 7,510,870 B2
(45) Date of Patent: Mar. 31, 2009

(54) STAT3 ACTIVATED STEM CELL

(75) Inventor: Il-Hoan Oh, Seoul (KR)

(73) Assignees: Industry-Academic Cooperation Foundation,, Seoul (KR); The Catholic University of Korea, Seoul (KR)

( * ) Notice: Subject to any disclaimer, the term of this patent is extended or adjusted under 35 U.S.C. 154(b) by 0 days.

(21) Appl. No.: 10/369,053

(22) Filed: Feb. 18, 2003

(65) Prior Publication Data
US 2003/0157711 A1   Aug. 21, 2003

(30) Foreign Application Priority Data
Feb. 15, 2002   (KR) .................... 10-2002-0008272

(51) Int. Cl.
C12N 5/00 (2006.01)
C12N 5/10 (2006.01)
C07K 14/435 (2006.01)

(52) U.S. Cl. ................... 435/325; 435/372; 530/350

(58) Field of Classification Search ............... 435/325, 435/355, 372, 377; 530/300, 350
See application file for complete search history.

(56) References Cited

U.S. PATENT DOCUMENTS 6,235,873 B1   5/2001   Bromberg et al. ........... 530/300

OTHER PUBLICATIONS

Bromberg et al. STAT3 activation is required for cellular transformation by v-src. Molec Cell Biol 18(5): 2553-2558, 1998.*
Bromberg et al. STAT3 as an oncogene. Cell 98: 295-303, 1999.*
McLemore et al. STAT-3 activation is required for normal G-CSF-dependent proliferation and granulocyte differentiation. Immunity 14: 193-204, 2001.*
Schuringa et al. Constitutive Stat3, Tyr705, and Ser727 phosphorylation in acute myeloid leukemia cells caused by the autocrine secretion of interleukin-6. Blood 95(12): 3765-3770, 2000.*
Shimozaki et al. Involvement of STAT3 in the granulocyte colony-stimulating factor-induced differentiation of myeloid cells. J Biol Chem 272(40): 25184-25189, 1997.*
Lazzari et al. Long-term expansion and maintenance of cord blood haematopoietic stem cells using thrombopoietin, Flt3-ligand, interleukin (IL)-6 and IL-11 in a serum-free and stroma-free culture system. Brit J Haematol 112(2): 397-404, 2001.*
Wagers et al. Cell fate determination from stem cells. Gene Therapy 9: 606-612, 2002.*
Ballas et al. Adult bone marrow stem cells for cell and gene therapies: implications for greater use. J Cell Biochem Suppl 38: 20-28, 2002.*
Becker-Hapak et al. TAT-mediated protein transduction into mammalian cells. Methods 24: 247-256, 2001.*
Matsuda et al., 1999, *The EMBO Journal*, 18(15):4261-4269.
Roder et al., 2001, *Experimental Hematology*, 29:694-702.
Niwa et al., 1998, *Genes & Development*, 12:2048-2060.
Raz et al., 1999, *Proc. Natl. Acad. Sci.* USA, 96:2846-2851.
Koning et al., 2000, *Oncogene*, 19:3290-3298.
Oh and Eaves, 2002, *Oncogene*, 21:4778-4787.
Hole et al., 1996, *Blood*, 88(4):1266-1276.
Potocnik et al., 1997, *Proc. Natl. Acad. Sci.* USA, 94:10295-10300.
Muller and Dzierzak, 1993, *Development*, 118:1343-1351.
Danet et al., 2001, *Experimental Hematology*, 29:1465-1473.
Dorrell et al., 2000, *Blood*, 95(1):102-110.
Eglitis and Mezey, 1997, *Proc. Natl. Acad. Sci.* USA, 94(8):4080-4085.
Hanazono et al., 2002, *Gene Therapy*, 9:1055-1064.
Lagasse et al., 2000, *Nature Medicine*, 6(11):1229-1234.
Larochelle et al., 1996, *Nature Medicine*, 2(12):1329-1337. Abstract Only.
Orlic et al., 2001, *Nature*, 410:701-705.
Poulsom et al, 2001, *J. Pathology*, 195:229-235.
Sauvageau et al., 1995, *Genes & Development*, 9(14):1753-1765. Abstract Only.
Xu and Reems, 2001, *Transfusion*, 41:213-218.
Yang-Jo Chung, "Unique Effects of Stat3 on the Early Phase of Hematopoietic Stem Cell Regeneration", Blood, Aug. 15, 2006, pp. 1208-1215, vol. 108, No. 4, The American Society of Hematology, Washington DC, U.S.A.
Chakraborty A, Teardy DJ. "Stat3 and G-CSR-Induced Myeloid Differentiation". Leukemia Lyumphoma, Aug. 1998, p. 433-442, vol. 30 (5-6), Department of Medicine, University of Pittsburgh School of Medicine, Univeristy of Pittsburgh Cancer Institute, Pennsylvania, U.S.A.

* cited by examiner

Primary Examiner—Bridget E Bunner
(74) Attorney, Agent, or Firm—Joseph Hyosuk Kim; JHK Law

(57) ABSTRACT

Stem cells modified to express activated form of STAT3 by genetic modification or protein delivery, and stem cells co-cultured with cells expressing activated form of STAT3 exhibit increased ex-vivo expansion and enhanced in-vivo regeneration accompanied by net increase in stem cell self-renewal as compared to control group.

8 Claims, 7 Drawing Sheets

STAT3 ACTIVATED STEM CELL

BACKGROUND OF THE INVENTION

1. Field of the Invention

The present invention relates to modified stem cells. The present invention also relates to methods of modifying stem cells for the purpose of stem cell expansion in-vitro. The invention also further relates to methods of enhancing stem cell proliferation and self-renewal in-vivo. The invention further relates to regeneration of tissues by using the modified stem cells.

2. General Background and State of the Art

Stem cell therapy is a new approach for medical intervention for many intractable diseases. Two types of stem cells can be used for regeneration of tissues, adult-type stem cells and embryonic stem cells. Adult-type stem cells including cord blood stem cells, bone marrow-derived stem cells, pancreatic stem cells or hepatic stem cells are very limited in the numbers that can be obtained from given tissues.

The pluripotent adult-type stem cells have the capacity to self-renew themselves and undergo multi-lineage differentiation. However, molecular mechanisms regulating such self-renewal and expansion of adult-type stem cells, in particular, hematopoietic stem cells has been illuminating.

Hematopoietic stem cells are one type of adult stem cells best characterized for heterogeneity in pluripotency and ability to proliferate in-vivo and in-vitro.

The most primitive undifferentiated state of hematopoietic stem cells have capacity to self-renew themselves and give rise to multi-lineage long term repopulation after transplantation into irradiated recipients. These cells are identified and defined in the transplantation model as CRU (competitive repopulating unit) (Larochelle 1996)

Another class of progenitor cells involved in hematopoiesis is assessed by their ability to form spleen colony (CFU-S: colony forming unit-spleen), which has more differentiated phenotypes and short-term repopulating ability.

One limiting factor in optimizing stem cell therapy using these pluripotent stem cells is that they are very prone to differentiation and loss of stem cell properties, leading to net loss of stem cell numbers after manipulation. Strategy to expand these stem cells including cytokine-aided ex-vivo culture, or modification of genes that are involved in regulation of stem cell proliferation has been tried. However, ex-vivo culture tends to give rise to more differentiated phenotype of stem cells despite the net increase of total cell numbers (Danet 2001, Dorrel 2000, Xu 2001).

To circumvent these limitations, several approaches were made by applying genetic modification in the stem cells including growth factor receptors or transcription factors with variable degree of increase in stem cell activities achieved (Hanazono 2002, Sauvageau 1995).

Recent studies in stem cell differentiation has shown that adult stem cells have the ability to differentiate into unexpected tissue types as well as expected tissue types. For example, hematopoietic stem cells can differentiate into neuronal cells, liver cells, renal cells, heart muscle cells, vascular tissues as well as hematopoietic lympho-myeloid lineages (Eglitis 1997, Poulsome 2001, Lagasse 2000, Orlic 2000).

STAT3 is a signal transducing molecule triggered by activation of IL-6 family growth factors, and gp-130 receptor family. The molecule is composed of DNA binding domain near N-terminus, SH2 domain, and transactivation domain near C-terminus.

Upon receiving signal from gp-130 receptors, JAK2 kinase is activated, which then phosphorylates tyrosine residue of STAT3. STAT3 then undergoes dimerization and nuclear localization for further activation of target genes.

Recently, it was shown that STAT3 activity can be constitutively activated by substituting several amino acid residue with cysteine residues (named STAT3-C), which leads to formation of disulfide bridge to dimerize this molecule in the absence of tyrosine phosphorylation or serine phosphorylation. (Bromberg 1999)

It was shown that functional knock out of STAT3 genes leads to loss of self-renewal and differentiation in the embryonic stem cells, and that STAT3 function is required for maintenance of undifferentiated phenotype of embryonic stem cells. (Matsuda 1999, Niwa 1998)

However, it is less likely that molecular mechanisms regulating adult hematopoietic stem cells are similarly regulated as embryonic stem cells, since transplantation of embryonic stem cells does not give rise to new reconstitution of bone marrows, and those mechanisms for adult hematopoietic stem cells has been illusive.

Recently, it was reported that over expression of dominant negative form of STAT3 can suppress bone marrow repopulation by such genetically modified hematopoietic stem cells, thus first identifying STAT3 activation as a mechanism that is necessary for in-vivo repopulation of transplanted stem cells, which is unique to adult hematopoietic stem cells (Oh, 2002).

However, in this study, over expression of wild type STAT3 genes did not affect any stem cell activity for bone marrow reconstitution. Thus, the reference did not disclose or suggest stem cell expansion by genetic manipulation of STAT3.

U.S. Pat. No. 6,235,873 discloses a mutant of STAT3 (STAT3-C) to increase dimerization of STAT3 protein in cells. STAT3-C contains two cysteine residues in the C-terminus of the protein in SH2 domain. However, the '873 patent does not disclose or suggest stem cells and related progenitor cells and their functional modulation of regenerative activities.

Matsuda et al. EMBO Journal, 18, 15, 4261-4269 (1999) discloses that STAT3 activation is sufficient to maintain an undifferentiated state of mouse embryonic stem cells. Niwa et al., Genes & Development, 12, 13, 2048-2060 (1998) discloses that self-renewal of pluripotent embryonic stem cells is mediated via activation of STAT3. These references describe the role of STAT3 for maintaining undifferentiated state of embryonic stem cell. A dominant negative form of STAT3 (STAT3-F) and inducible form of STAT3 (STAT3-ER) was used to demonstrate the requirement of STAT3 activity in maintaining the undifferentiated phenotype of embryonic stem cells. However, these references fail to disclose or suggest that activated form of STAT3 enhance the STAT3 activities above the unmanipulated state. In addition, these references fail to disclose or suggest usage of adult stem cells or primary stem cells such as hematopoietic stem cells, nor their increased activities during in-vivo regeneration of tissues.

Oh et al., Oncogene July 18;21(31):4778-87 (2002) discloses that overexpression of dominant negative form of STAT3 suppresses the repopulating activity of hematopoietic stem cells. However, overexpression of wild-type STAT3 does not exert any effect on these stem cells. Thus, the reference fails to disclose or suggest that stem cell activity is enhanced by activated form of STAT3.

The present application describes exogenous expression of activated form of STAT3 (exemplified with STAT3-C) leads to net expansion of stem cells with increase in their self-renewal and regenerative capacity.

SUMMARY OF THE INVENTION

In one aspect, the invention is directed to method for increasing self-renewal and in-vivo/in-vitro proliferation of stem cells resulting in enhanced regeneration of tissues or organs. By increasing STAT3 activity in the stem cells, the stem cells exhibit higher self-renewal with higher content of undifferentiated stem cells, and enhanced regenerative activity.

Increase of STAT3 activity by introducing active form of STAT3 gene (exemplified with STAT3-C) or by protein delivery of such proteins (exemplified with His-TAT-STAT3-C fusion protein) into the stem cells exerted similar effect on stem cells to enhance proliferative and regenerative activities.

Therefore, stem cell expansion and enhancement of regenerative function can be achieved either by gene therapeutic approach or by protein therapy.

This increase of stem cell proliferative capacity was also achieved by culturing stem cells with mesenchymal stem cell feeder layers that express activated form of STAT3 (exemplified with STAT3-C).

The increase in proliferative and regenerative function occurred both during in-vitro cultivation and during in-vivo regeneration, allowing for both ex-vivo expansion of stem cells and method to enhance in-vivo regeneration and/or selective expansion of particular stem cell population modified by aforementioned methods.

In a preferred embodiment, the stem cell is a hematopoietic stem cell. In a more specific embodiment, the hematopoietic stem cell is a human hematopoietic stem cell expressing the cell surface marker CD34 or c-kit and includes hematopoietic stem cells that can differentiate into non-hematopoietic tissues including liver, heart, kidney, or nervous tissues.

In another aspect of the invention, stem cell activity is enhanced by increasing STAT3 activities, and any pharmacological intervention or natural ligands aimed at modulation of STAT3 activities may be used to manipulate proliferative and regenerative activities of stem cells.

Thus, the present invention is directed to a method for manipulating stem cell to increase stem cell self-renewal and expansion with multiple approaches aimed at modulating STAT3 activities.

The invention is directed to a modified stem cell comprising activated form of STAT3. The modified stem cell may have increased in-vitro proliferative activity while maintaining multipotent characteristics of unmodified parental cell. Further, the modified stem cell may be a hematopoietic stem cell. The modified stem cell may be a multipotent stem cell that can differentiate into non-hematopoietic cell as well as into hematopoietic cell. The cell may be a mammalian stem cell, preferably a human stem cell, and may be optionally obtained from umbilical cord blood. Further, the STAT3 may be STAT3-C.

The invention is also directed to a modified stem cell described above, wherein the protein products of constitutively activated STAT3 is delivered into cells by protein transduction.

The invention is also directed to a method of making the modified stem cell described above, comprising transducing the cell with activated STAT3 gene. In the method above, the STAT3 gene is STAT3-C gene, and the modified stem cell may be made by delivering STAT3 polypeptide into the cell. In this method, the STAT3 is STAT3-C.

The invention is also directed to a method of expanding stem cell population comprising allowing the modified stem cell described above to proliferate. The cell population may be ex-vivo, in-vivo, or in-vitro. The method may further comprise contacting the stem cell with a chemical substance to increase STAT3 activity. In one aspect, the chemical substance may be a STAT3 dimerizing compound or STAT3 dimerizing mutation. In another aspect, the method may comprise co-culturing cells expressing activated STAT3 with a stem cell population.

The invention is also directed to a method of accelerating engraftment after transplantation in a subject comprising administering the modified stem cell described above to a subject in need thereof. In another aspect, the invention is directed to a method of regenerating tissue in a subject comprising administering the modified stem cell described above to a subject in need thereof.

In still another aspect, the invention is directed to a method of recovering bone marrow in a patient suffering from loss of bone marrow cells, comprising administering the above-described modified stem cell to a subject in need thereof.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 5B shows a vector construct for expression of the protein.

DETAILED DESCRIPTION OF THE PREFERRED EMBODIMENTS

Figure 1:
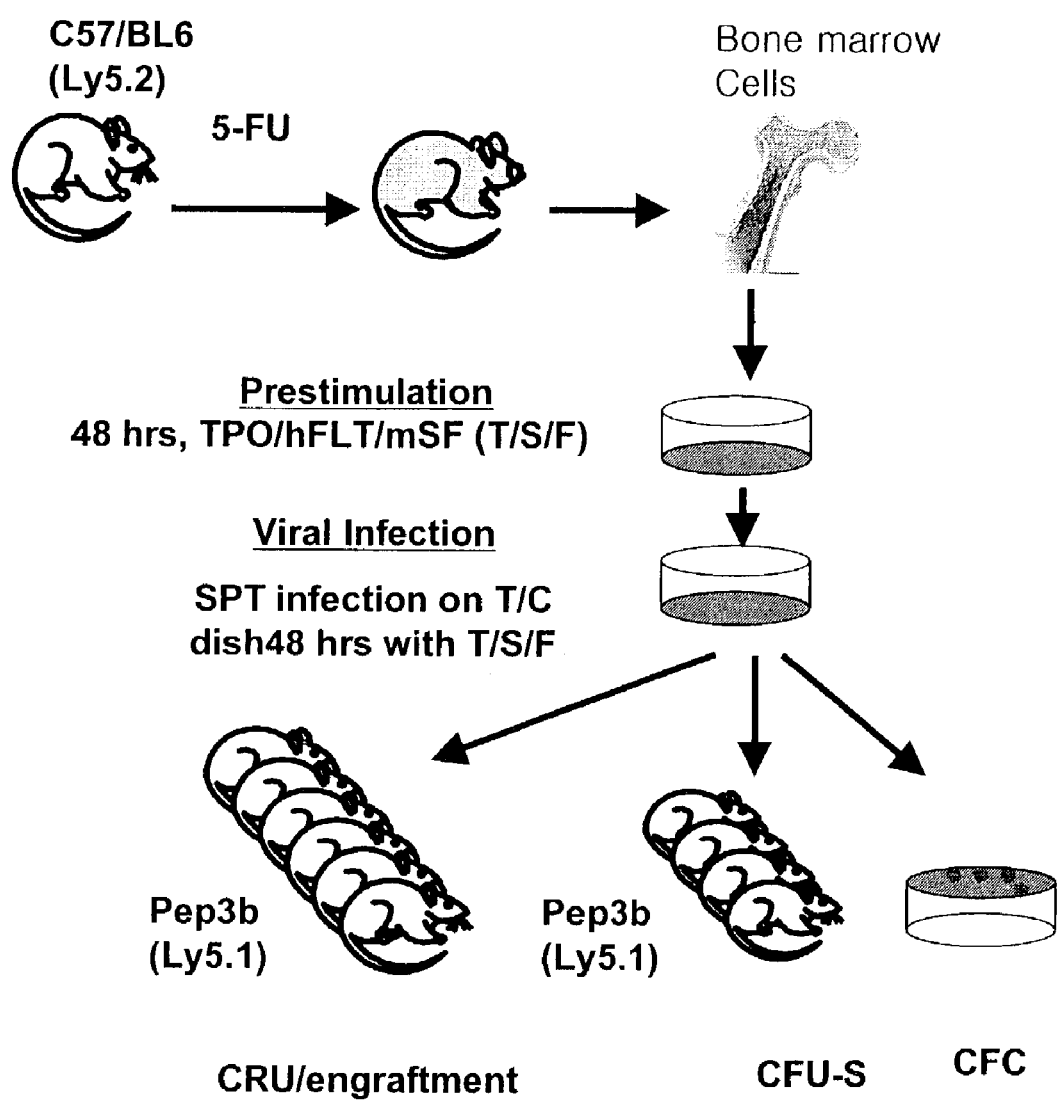
FIG. 1 shows a diagram of experimental strategy to study effect of STAT3 activity on various stages of hematopoietic stem cells. Donor cells with surface markers of Ly5.2 (C57BL6) were enriched with progenitor cells by pretreatment with 5-FU for four days and bone marrow cells were harvested. The cells were prestimulated and infected with virus harboring various mutants of STATs and transplanted into irradiated recipients (Pep3b:surface marker Ly5.1) and assayed for their ability to engraft and reconstitute the recipients' bone martow. Simultaneously, aliquots of transduced cells were transplanted into recipients for their ability to form spleen colony (CFU-S) at post-transplantation 12 days, or cells were plated onto methylcellulose plates for their ability to form colony on the plates.

In the present application, "a" and "an" are used to refer to both single and a plurality of objects.

Before the present invention and methods for using same are described, it is to be understood that this invention is not limited to the particular cell type, STAT3-C gene, or methodology that are exemplified. It is also to be understood that the terminology used herein is for the purpose of describing particular embodiments only and is not intended to be limiting.

Definitions

As used herein, "activated STAT3" refers to a variety of modifications to STAT3 such that stem cell proliferation activity is increased. Such activation may occur by dimerization of STAT3. Another method includes phosphorylation of STAT3. For instance, STAT3 is phosphorylated upon activation at tyrosine (705 residue) and serine residues (723 residue). It is also known that certain phosphatases dephosphorylate it quite rapidly. Thus, inhibition of this STAT3-specific phosphatase may increase STAT3 activity. Other methods of activating STAT3 may include contacting cells with a chemical that inhibits a negative regulator of STAT3 activation. For instance, SOCS family gene (SOCS-1 to SOCS-6) is suggested to play a role in negative regulation of STATs. Thus, inhibiting SOCS gene family may activate STAT3.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the STAT3 polypeptide or variants of the present invention may contain any number of amino acids or alterations of amino acids in STAT3, including substitutions and/or insertions and/or deletions in any region of the polypeptide or the gene encoding STAT3, so long as the STAT3 polypeptide or variant is activated and promotes proliferative activity of the stem cells which harbor activated STAT3 polypeptide or the gene encoding activated STAT3 polypeptide. The variant STAT3 protein or DNA may include a sequence that is at least about 70%, 75%, 80%, 85%, 90%, 95%, 96%, 97%, 98% or 99% identical to the polypeptide or DNA sequence of known STAT3 sequence.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of a native polypeptide such as STAT3 or a fragment thereof with an organic proteinaceous or non-proteinaceous derivatizing agent, and post-translational modifications. Activation of STAT3 is desired by such covalent modifications. Such activation may occur by dimerization of STAT3. Another method includes phosphorylation. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide.

As used herein, "effective amount" is an amount sufficient to effect beneficial or desired clinical or biochemical results. An effective amount can be administered one or more times. For purposes of this invention, an effective amount is the amount of a compound that activates STAT3 or an amount of activated STAT3 necessary for enhanced proliferative activity stem cells. In yet another embodiment, the "effective amount" is defined as the amount of the activated stem cells that is effective to regenerate tissue.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "purified" or "isolated" molecule refers to biological molecules that are removed from their natural environment and are isolated or separated and are free from other components with which they are naturally associated.

As used herein, "sample" or "biological sample" is referred to in its broadest sense, and includes any biological sample obtained from an individual, body fluid, cell line, tissue culture, or other source which may contain stem cells, depending on the type of assay that is to be performed.

As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment. Typically, the "treatment" entails administering activated or modified stem cells to the patient to regenerate tissue.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

As used herein, "stem cell" refers to a cell with capability of multi-lineage differentiation and self-renewal, as well as the capability to regenerate tissue. Although stem cells are described mostly with respect to hematopoietic stem cells in the present application, the invention is not limited to such and may include stem cells of other origin, including but not limited to stem cells from liver, pancreas, neuron, and bone marrow mesenchymal stem cells.

As used herein, "engraftment" and "in-vivo regeneration" refer to the biological phenomenon, in which implanted or transplanted stem cells produce differentiated cell progeny as well as themselves in the body, and/or replace lost or damaged cells with injected cells.

As used herein, "CRU (competitive repopulating unit)" refers to a unit to measure long-term engrafting stem cells, which can be detected after in-vivo transplantations.

As used herein, "modified stem cell" or "activated stem cell" refers to a stem cell into which exogenous genetic material has been inserted into the cell, and in some instances incorporated into its genome as well as exogenous protein products delivered into the cells.

Stem Cells

Stem cells differ from other kinds of cells in the body. All stem cells—regardless of their source—have three general properties: they are capable of dividing and renewing themselves for long periods; they are unspecialized; and they can give rise to specialized cell types. Relating to their long-term self-renewal, embryonic stem cells proliferate for a year or more in the laboratory without differentiating, but most adult stem cells cannot.

Stem cells have been frequently cultivated in the culture medium containing multiple cytokines. However, it has been observed from many experiments that while these techniques lead to net increase in the total nucleated cells, such ex-vivo expanded stem cells undergo differentiation and lose stem cell properties (Danet 2001, Dorrel 2000, Xu 2001). Reasons for this loss of stem cell content during cultivation can be partially attributed to asymmetric cell division where undifferentiated stem cells produce more differentiated daughter cell progenies. In addition, cell surface phenotypes change during ex-vivo cultivation process. For example, CD34+38+ cells, which represent a more differentiated population compared with CD34+CD38− cell population, takes phenotypes of CD34+CD38− cells due to loss of CD38 expression, thus phenotypically resembling expansion of primitive CD34+CD38− cells, but without actual increase in transplantable stem cells as reflected by the extent of in-vivo reconstitution (Dorrel 2000).

The results of these differentiative loss of stem cells is decrease in engraftment and in-vivo repopulation by stem cell transplantation.

These trials include human CD34+ cells cultivated in the bioreactors for clinical grade expansion, where net losses of transplantable stem cells were observed.

Classical study on primitive hematopoiectic stem cells have been reflected with CRU (competitive repopulating unit) that has capacity to regenerate the bone marrow cells after irradiation (Larochelle 1996).

Although CRU has been shown to undergo stochastic behavior on their self-renewal, it has been shown that a certain combination of cytokine mixtures tends to cause higher probability of self-renewal than other cytokine conditions (Zandstra 1997). This observation suggests that there exists a certain signal that can lead to self-renewal of hematopoietic stem cells and ex-vivo expansion based on molecular manipulation. However, little have been known for molecular mechanisms of self-renewal nor mechanisms maintaining undifferentiated status of primitive hematopoietic stem cells.

Although STAT3 has been known to be required to maintain undifferentiated status of embryonic stem cells, significant distinction exist between embryonic stem cells and adult-type hematopoietic stem cells. First, embryonic stem cells do not regenerate the bone marrow with lympho-myeloid repopulation, that argues that embryonic stem cells and adult hematopoietic stem cells are two different class of stem cells. Secondly, molecular environment of embryonic stem cells are different from adult hematopoietic stem cells. For example, most characteristic markers for embryonic stem cells are expression of stage specific antigens (SSEAs) and transcription factor Oct-4, but both of these genes are not expressed in adult hematopoietic stem cells (our data). Therefore, molecular mechanisms for hematopietic stem cells to engraft and reconstitute bone marrow with multi-lineage differentiation should be a unique situation for hematopoietic stem cells and can not be learned from any other cell types.

Recently, it was discovered that STAT3 expression level in primitive cell population of human bone marrow is maintained at a higher level than those observed for more downstream stages of differentiated progenitor cell population. In addition, it was discovered that retroviral expression of dominant negative form of STAT3, which can inhibit endogenous STAT3 activating pathway, profoundly suppresses the repopulating activities of transplanted stem cells derived from murine fetal liver.

The present application shows that the ability of primary hematopoietic stem cells to engraft and repopulate the recipients' bone marrow is directly regulated by STAT3 activity, and furthere applicants have demonstrated that proliferative and repopulating ability of primary hematopoietic cells are significantly enhanced by increase of STAT3 activities.

Therefore, unlike the classical view that stem cell behavior is regulated in a stochastic manner, now it has been discovered that stem cell behavior may be modified by manipulating STAT3 activities in the cells. This is achieved by 1) genetic modification, 2) protein transfer of activated form of STAT3, or 3) pharmacological intervention that can change the molecular activities of STAT3 gene products.

By employing these methods, primary stem cells are expanded during in-vitro cultivation or during in-vivo regeneration for net increase in efficacy of stem cell transplantation, and for selective amplification of particular cell subsets when it is desired for gene therapeutic considerations as detailed below.

Enhancing in-vivo Regeneration by Stem Cells

Hematopoietic stem cells for autologous transplantation may be removed from a subject by aspiration or by mobilization for gene transfer of STAT3-C genes using direct transfection or various viral vectors.

After the patient is treated with chemotherapy or radiation therapy, the modified stem cells are re-injected into the body, and modified stem cells show accelerated engraftment and repopulation of bone marrow shortening the time of aplastic window, thus decreasing the transplantation related mortality.

Alternatively, the removed stem cells are incubated in a culture medium that contains STAT3-C protein which has a protein transduction domain and is reinjected into the subject. The form of STAT3 protein delivered into the cells increases the ability of the cells to self-renew and reconstitute in bone marrow. Our study shows that TAT-STAT3-C protein transferred protein have higher repopulating ability (two to five fold) as compared to control groups transferred by TAT-GFP protein only. Therefore, this approach may be successfully used to enhance the regenerative capacity of stem cells by protein therapy targeted to STAT3 activity.

In addition, the protein may be directly injected into the subject, wherein the protein is delivered into stem cells, wherein they effectuate in-vivo regenerative activities.

Selective Expansion of Particular Stem Cell Population

In human beings suffering from genetic disease caused by somatic mutation such as thalassemia or congenital metabolic disease, stem cells producing all lineages are removed from a subject, and genetic correction is performed. When these cells are reintroduced into the body, genetically corrected cells would not have any selective advantage over uncorrected cells and therapeutic reconstitutive effect would be decreased by competition between these two populations.

But, using the inventive method, the particular stem cells with genetic modifications can be further modified to express activated form of STAT3, then these modified cells have selective advantages over un-modified stem cells resulting in net increase in the portion of cells genetically corrected.

Inducible Expansion of Stem Cell Proliferation in-vivo by Chemical Dimerizers

STAT3 activity is a direct regulator of stem cell regeneration. Thus, stem cell behavior may be induced. By making fusion genes between STAT3 and FKBP binding protein, or dimerizing domain of DNA gyrase B, (Brino, 2000), STAT3 could be induced to dimerize in the presence of a chemical such as FK1012 or coumermycinA1. After stem cells are transduced by a fusion gene comprising STAT3 and dimerizing domain, the stem cells are reinfused into the subject. When the subject is treated with dimerizing agent such as FK1012, or coumermycinA1, the chimeric STAT3 protein is dimerized and exerts its proliferative effect only in the modified stem cells. In the absence of a chemical dimerizer, it would not be dimerized hence, stimulatory effect of STAT3 will subside. In this fashion, stem cell activities of in-vivo transplanted stem cells can be controlled by exogenous administration of dimerizing agents.

Ex-vivo Expansion and Maintenance of Stem Cell Properties

Many stem cells need to be modified in-vitro after being withdrawn from subject. Such a situation includes ex-vivo expansion of stem cells to increase the total amount of stem cells. In addition, stem cells may be genetically modified or chemically treated to achieve functional changes and often subject to ex-vivo manipulations such as gene transfer by viral vectors, treatment with anti-sense oligonucleotides, or cytokines. During these processes, stem cells easily lose their stem cell properties, and also decrease in number. Here, by using the protein products of activated STAT3 (STAT3-C exemplified) fused to protein transduction domain, the cells can be better maintained with their self-renewing and regenerative capacity. Alternatively, chemicals or natural ligands that increase STAT3 activity may be used for the aforementioned purpose.

In another aspect, the invention is directed to removal of tumor cells contaminated in the bone marrow. Cancer or leukemia patients generally need chemotherapy or radiation therapy, which are toxic to bone marrow cells. Bone marrow cells are removed for later reinfusion and anti-cancer treatment is applied. During the interval, contaminated tumor cells are removed by either surface marker selection on normal stem cells or by using cytotoxic, radioactive chemicals etc. During this process, stem cells can be better maintained by employing the aforementioned strategy to increase STAT3 activities in stem cells by protein transduction or chemical treatment increasing activity of the molecule.

Gene Therapy

In a specific embodiment, nucleic acids comprising sequences encoding the STAT3 polypeptide are administered to activate stem cells, which may be used to proliferate stem cells and regenerate tissue by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode STAT3 polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the STAT3 encoding nucleic acids.

Delivery of the nucleic acids into a patient may be either direct, in which case the patient is directly exposed to the nucleic acid or nucleic acid—carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient, but also includes allogeneic donor cells.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day of a STAT3 activator or activated STAT3 gene or proteins may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendritic cells sensitised in vitro and adoptively transferred to the recipient). Depending on the route of administration, the peptide may be required to be coated in a material to protect it from the action of enzymes, acids and other natural conditions which may inactivate said ingredients.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The present invention is not to be limited in scope by the specific embodiments described herein. Indeed, various modifications of the invention in addition to those described herein will become apparent to theose skilled in the art from the foregoing description and accompanying figures. Such modifications are intended to fall within the scope of the appended claims. The following examples are offered by way of illustration of the present invention, and not by way of limitation.

EXAMPLES

Example 1

Materials and Methods

Animals: Congeneic mice used as a bone marrow donor were 8-12 wk Peb3b/C57/BL6 (surface marker: Ly5.1) and recipients were C57/BL6 (surface marker: Ly5.2).

These mice were bred in the animal facility unit of Catholic University of Korea in sterile micro-isolator cages with sterilized food and water.

Cloning and Retrovirus Production

STAT3-C was constructed by site-directed mutagenesis starting from wild-type STAT3 cDNA as described previously (Bromberg et al. 1999). Dominant negative form of STAT3 was kindly provided by Dr. Allice Mui (University of British Columbia, Canada). These cDNAs were cloned into MIG vector using EcoR1 and Xho1 site in the multiple cloning site.

Figure 2:
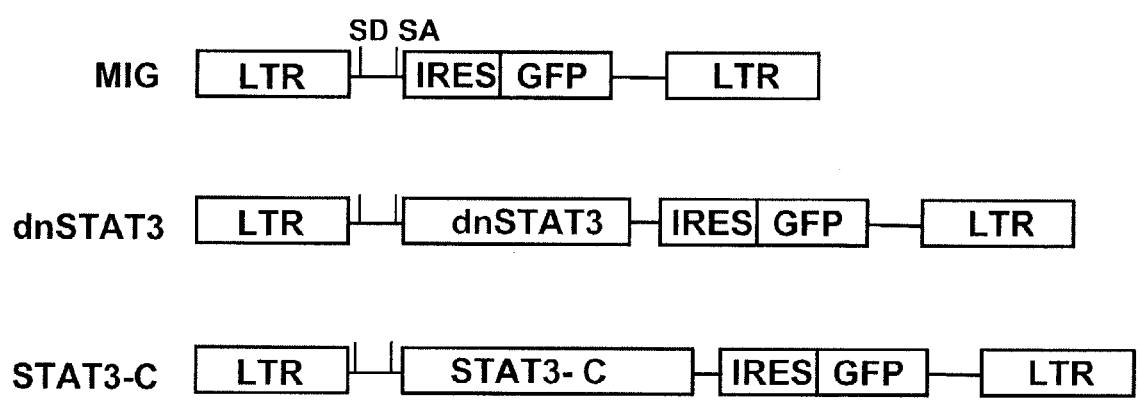
FIG. 2 shows schematic diagram of retroviral constructs for dominant negative STAT3 (dnSTAT3) or activated STAT3 (STAT3-C). Each cDNA was cloned into retroviral vector, MIG (MSCV-IRES-GFP), where each cDNAs are connected to GFP with IRES (internal ribosomal entry site) and expression of each gene is monitored by expression of GFP gene due to simultaneous expression of both genes.

The retrovirus MIG (MSCV-IRES-GFP) is driven by LTR from murine stem cell virus (kindly donated by Dr. R. Hawley, American Redcross). The multiple cloning site of this vector is connected to EGFP (enhanced green fluorescent protein, Clontech, CA) with IRES (internal ribosomal entry site) so that expression of cloned gene is connected to expression and therefore detection of EGFP by fluorescence (FIG. 2)

After cloning, retrovirus was produced by co-transfecting retroviral construct, plasmid encoding gag-pol (GP3, kindly provided by Dr. Rob Kay, Terry Fox Lab, Vancouver, Canada), and plasmid for envelope (VSV-G) into 293 T cells by calcium phosphate transfection method. At post-transfection 48 hrs, the viral supernatant was collected and concentrated using ultracentrifugation at 25,000 RPM for 1 hr. The concentrated viral particles were used to infect GPE-86 producer cells or PG13 cells, the viral supernatant thus prepared was used to infect bone marrow cells in the presence of protamine sulfate (5 ug/ml).

Retroviral Transduction and Bone Marrow Transplantation

FIG. 1 represents the experimental design to analyze the regenerative capacity of hematopoietic stem cells at various stages of hematopoiesis.

Mice were treated with 5-fluorouracil, and bone marrow cells were harvested four days after the treatment. At this point un-differentiated, progenitor cells are enriched due to selective toxicity of 5-FU on cycling cells.

The donor cells were then prestimulated in serum free media in the presence of cytokine mixtures (thrombopoietin 50ng/ml, flt3-ligand 100 ng/ml, steel factor 100 ng/ml) for 48 hrs, then transduced by retroviral particles three times over 48 hrs in the same conditions as for pre-stimulation, then transplanted into recipients.

For transplantation of transduced donor cells, recipients were irradiated (900 rad) and transplanted within 24 hrs of irradiation, then provided with acid water (pH3.0) for 3 weeks.

Repopulation by transplanted donor cells was quantitated using recipients' peripheral blood at various time points after transplantation. Using specific antibodies, the % of donor cells (%Ly5.2 in the recipient) was calculated using flow-cytometry (FACS Caliber, Beckton Dickinson)

In addition, the transduced stem cells were transplanted simultaneously for day 12 CFU-S and colony forming assay in the methyl-cellulose plates.

Example 2

Enhancement of Stem Cell Activities by Activated Form of STAT3

The effect of altering STAT3 activities in the bone marrow stem cells were tested by transplanting donor cells transduced by dominant negative STAT3 (dn-STAT3), activated STAT3 (STAT3-C) along with cells transduced by control vector (MIG).

50,000 of each input cells were transduced by above mentioned methods, and gene transfer efficiency assessed by GFP was 85-90%. These cells were transplanted into recipient mice (Pep3b, Ly5.1) and engraftment and repopulation of bone marrow was analyzed by % donor cells with GFP positive cells in the recipient's peripheral blood at various time points.

FIG. 3 shows the effect of transducing each viral constructs on their stem cell activity in bone marrow regeneration.

Figure 3A:
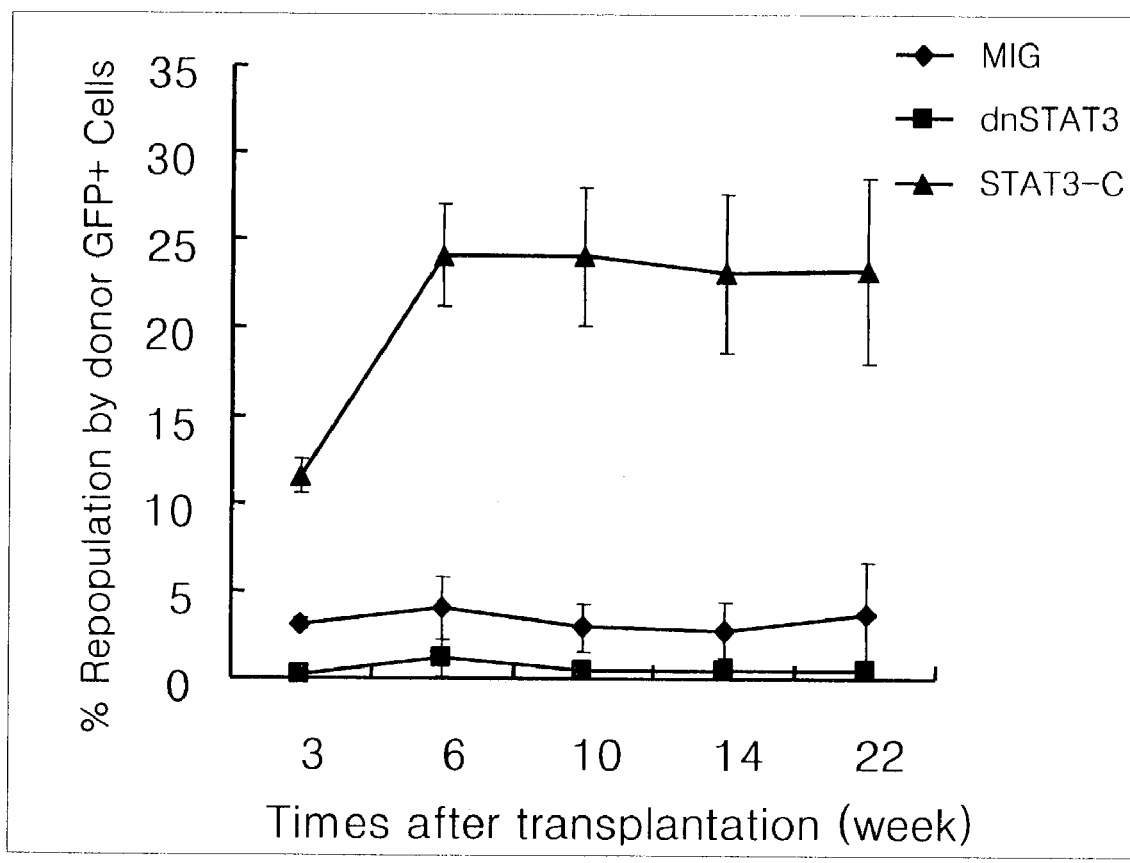
FIG. 3A shows effect of altering STAT3 activities in hematopoietic stem cells on their engraftment and in-vivo regeneration of bone marrow. Hematopoietic stem cells obtained from 5-FU treated bone marrow were transduced with retrovirus (MIG) encoding dn-STAT3 or STAT3-C along with control vector, and transplanted into irradiated recipients. The gene transfer efficiency of each viral construct was 85-90%. At various time points after transplantation, peripheral blood of recipients were analyzed for donor cell engraftment and effect of altering STAT3 activities by analyzing % of Ly5.2 (donor cells) and % GFP (transduced cells). As shown in the figure, cells with decreased STAT3 activities (dn-STAT3) have lower engraftment and repopulation as compared to control group, but cells with higher STAT3 activities (STAT3-C) shows markedly enhanced in-vivo regeneration.

As shown in FIG. 3A, transduction of activated form of STAT3 (STAT3-C) results in significant increase in donor cell engraftment 5 to 10 fold above the control groups (P<0.05). The enhanced in-vivo repopulation of STAT3-C transduced cells started to be apparent as early as post-transplantation 3 week point, showing that it could accelerate the process of engraftment by transplanted donor cells.

Interestingly, increased ability of STAT3-C transduced cells did not lead to continued increase in the repopulation reaching plateau at post-transplantation 6 week points. Thus, enhancement of in-vivo regenerative capacity of stem cells by STAT3 activation does not lead to leukemic condition, rather regulated by normal physiological feed back control after reaching stationary period of regeneration.

In contrast, transduction of dominant negative form of STAT3 (dn-STAT3) resulted in significant decrease in the bone marrow regeneration (P<0.05) compared to control group, showing that inhibition of STAT3 activities in the cell can suppress in-vivo repopulating activities of transplanted stem cells.

Figure 3B:
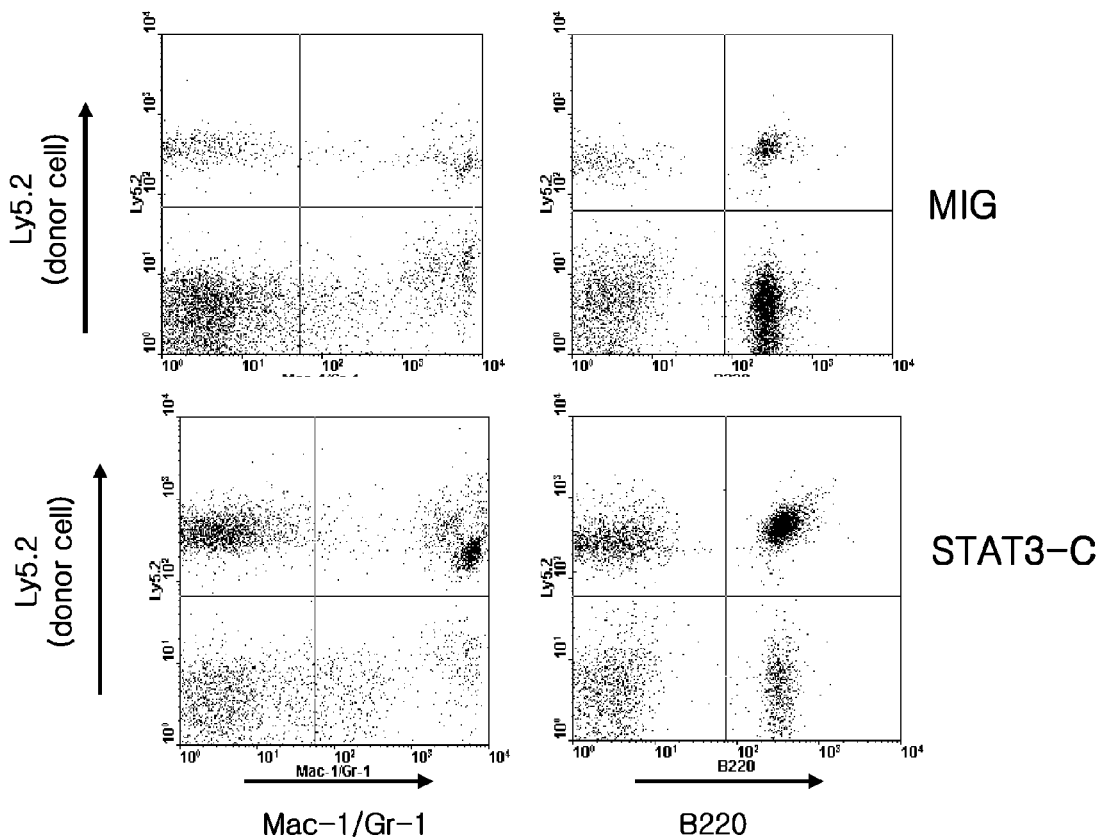
FIG. 3B shows multi-lineage differentiation of STAT-C transduced cells. Donor-derived STAT3-C transduced cells were analyzed for their differentiation into lymphoid and myeloid lineage using surface marker for B-lymphoid (B220 antibody) and myeloid (Mac-1/Gr-1 antibodies) cells. As shown in the figures, SAT3-C transduced hematopoietic stem cells retain their ability to differentiate into both myeloid and lymphoid lineages without deviation to a particular lineage. These data show that increased engraftment shown in FIG. 3-A is not due to selective proliferation of a particular lineage, rather it is due to increase in stem cell level that has capability to differentiate into multiple lineages.

In order to see whether STAT3-C transduced cells retain capacity for multi-lineage differentiation, lineage distribution of cells derived from STAT3-C transduced cells were analyzed. FIG. 3B is a representative analysis of lineage distribution as depicted by lymphoid (B220) and myeloid (Mac-1/Gr-1) cells. As shown in the figures, STAT3-C transduced cells can differentiate into both lymphoid and myeloid lineages without deviating a particular lineage. This result shows that the enhanced repopulation of bone marrow by STAT3-C transduced cell is not due to clonal proliferation of a particular lineage cells, but rather, it is due to enhancement of regeneration at the primitive multi-potent stem cell level.

Example 3

Effect of Altering STAT3 Activity on CFU-S and CFCs

To test whether STAT3-C mediated enhancement of bone marrow repopulation also occurs during other stages of hematopoietic cell differentiation, observations were made of CFU-S at day 12, which reflects the immediate downstream stage of stem cell differentiation from multi-potent stem cells, and CFC that reflects oligo-clonal precursor cells further downstream of CFU-S.

Figure 4:
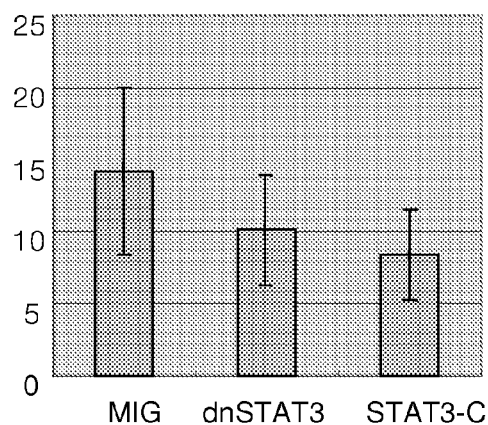
FIG. 4 shows effect of increasing STAT3 activity on other stage of hematopoietic progenitors. Bone marrow cells transduced with dn-STAT3, STAT3-C or control vector were transplanted into irradiated mice for CFU-S on day 12 or plated onto methylcellulose semi-solid culture media for colonogenic CFC assay. As shown in the figure, no significant changes were observed for CFU-S or CFC transduced by each viral construct. These data shows that expression of STAT3-C or dn-STAT3 selectively modulates primitive transplantable stem cell activities without affecting further downstream stages of hematopoietic cells.
Figure 4:
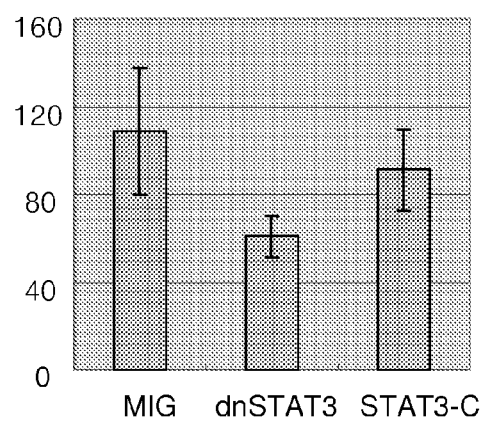

As shown in FIG. 4, no significant changes were observed in day 12 CFU-S or CFCs, thus showing that STAT3 activity does not affect other stages of hematopoietic stem cells. Therefore, activation of STAT3 increases bone marrow repopulation by selectively up-regulating stem cell activity without affecting any of downstream progenitor cells, and the increase observed in repopulation directly reflects the enhancement of stem cell activities.

Example 4

Protein Therapy to Increase Stem Cell Activity and ex-vivo Expansion

Although transduction of genes encoding activated form of STAT3 is a reliable method to increase STAT3 activities in the cells, delivering the protein products of activated STAT3 should be an alternative way of increasing intra cellular STAT3 activities.

Figure 5A:
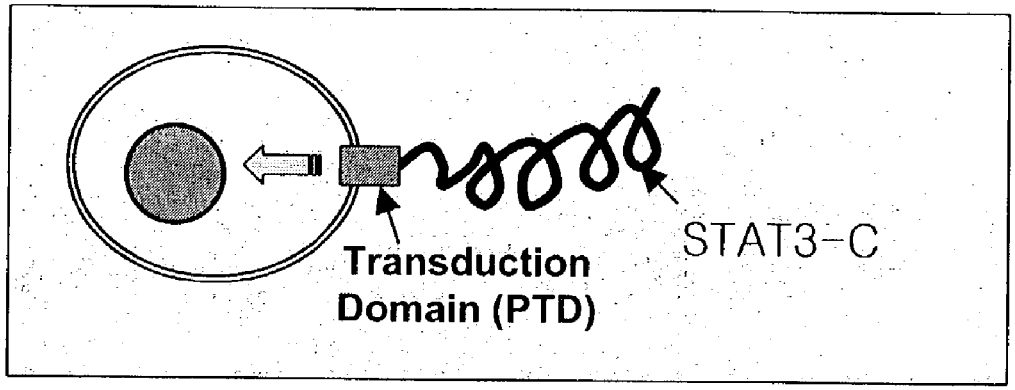
FIGS. 5A and 5B show schematic diagram for protein therapy of hematopoietic stem cells for ex-vivo expansion or enhancement of in-vivo regeneration. The protein product of activated STAT3 (STAT3-C exemplified here) was fused to protein transduction domain (using TAT sequence of HIV) and six histidine residues. This chimeric protein penetrates through cell membrane and is delivered into cells and may result in increased STAT3 activity in the cells. In addition, injection of this protein into mammalian body exerts similar effect of increasing STAT3 activity in the stem cells.
Figure 5A:
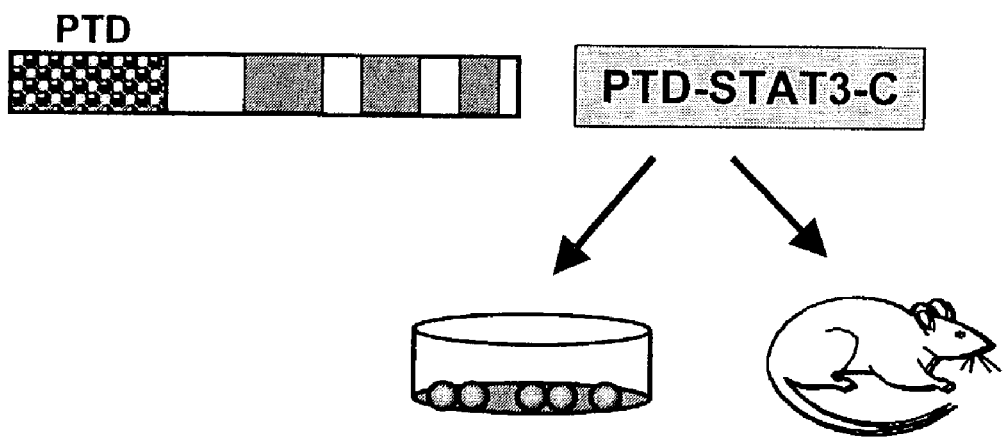
Figure 5B:
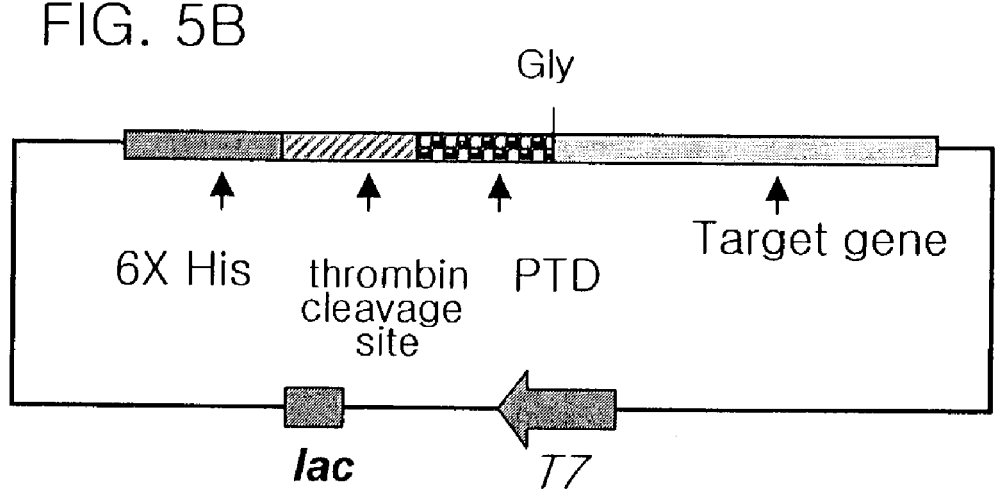

The protein products exogenously added can be delivered into the cells by fusing protein transduction domain (PTD) such as the membrane penetrating domain (9 amino acids) from TAT sequence in HIV (as schematically illustrated in FIG. 5).

The chimeric protein that has 6 histidine residue, TAT and STAT3-C was produced in bacteria and purified by Ni-NTA column. Bone marrow cells obtained from 5-FU treated animal was cultivated in the presence of cytokine mixtures (thrombopoietin, steel factor, flt-3 ligand at concentration aforementioned) and protein products of HIS-TAT-STAT3-C (1 ug/ml) or TAT-GFP protein (1 ug/ml).

After 5 days of culture, the cells were transplanted into irradiated animal as described and analyzed for donor cell repopulation at 3 week and 6 weeks. From these experiments, TAT-STAT3-C transduced cells showed 2-5 fold enhancement of regenerative activity as compared with control group, thus showing that the goal of "increasing STAT3 activity in the cell" can be also achieved by protein therapy using protein products of activated STAT3 fused to protein transduction domain.

Example 5

In-vivo Self-Renewal of Transplanted Stem Cells

In order to determine whether enhanced stem cell activities include enhanced self-renewal of transplantable stem cells in-vitro, the cells transduced by GFP and by STAT3-C were serially transplanted into mice at 48 hrs of infection. In addition, to see the self-renewal of transplanted stem cells in-vivo, the cells to be transplanted into primary recipients were serially diluted and transplanted into at least 6 mice at each dose to determine the CRU frequency in each case. After 36 weeks of transplantation into primary recipients, the engrafted cells were again harvested from primary mice and transplanted into secondary mice with similar serial dilution to measure the number of CRUs produced in primary recipients during in-vivo regenerations.

Figure 6:
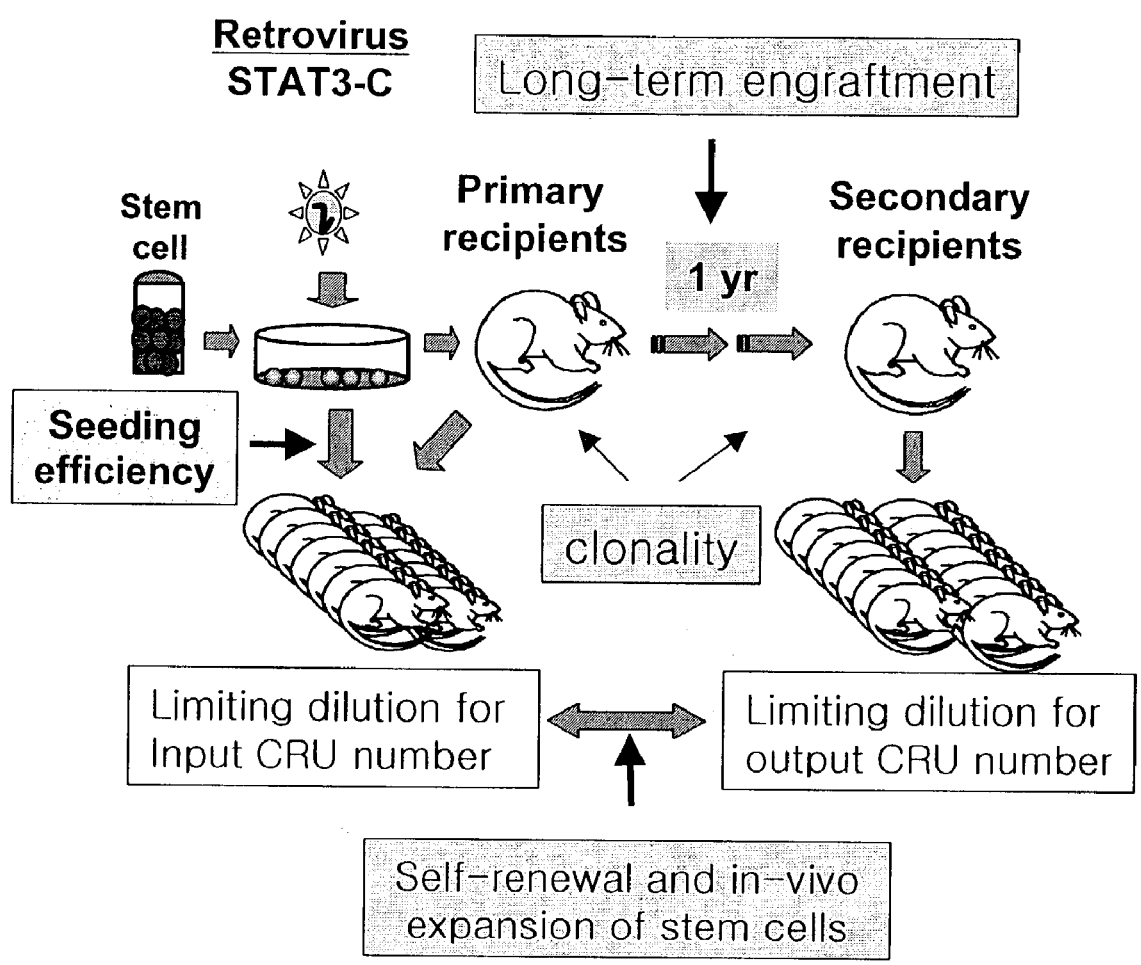
FIG. 6 shows quantitation of self renewal and stem cell expansion in-vivo. Test cells were transduced with STAT3-C and transplanted into at least 6 irradiated recipients at three different cell doses. Donor cell repopulation was assessed in these transplanted mice. Cell dose giving negative engraft (<1% donor cells in lymphoid or myeloid cells) in 37% of tested animals is defined as one CRU (competitive repopulating unit). The primary recipients' bone marrow is again harvested at 36 weeks post-transplantation and transplanted into secondary recipients after serial dilution until the dose reaches limiting dosage (<37% of animal with negative engraftment) and total numbers of CRU transplanted into the primary recipients and CRU numbers transplanted from primary mice into secondary mice is calculated.

FIG. 6 represents schematic illustration of experimental design to measure the changes in stem cell content as reflected by changes in CRU frequency.

From these experiments, CRU frequency was obtained and are listed in Tables 1 and 2. As shown in Table 1, the number of CRU in $1 \times 10^6$ cells in the STAT3-C transduced cells reached 20 CRUs while cells transduced by GFP reached 14 CRUs. Since the cells were transplanted 48 hrs after viral infection, this result shows that even with a culture time period of less than 48 hrs, significant increase in CRU (or stem cell numbers) can be achieved in-vitro. Therefore, increase of STAT3 activity can be used to induce self-renewal and ex-vivo expansion.

TABLE 1

CRU frequency after in vitro gene transfer culture

| Transplant type | CRU frequency (95% CI) | No. CRU/1 × 10$^6$ GFP$^+$ cells (95% CI) |
|---|---|---|
| STAT3C-GFP | 1/49,794 (1/18,474-1/134,209) | 20 (8-54) |
| GFP | 1/98,652 (1/24,438-1/398,235) | 14 (3-41) |

CI, confidence interval.

TABLE 2

CRU regeneration at 36 weeks post-transplant

| Transplant type | CRU frequency (95% CI) | No. CRU/2femurs & 2tibias (95% CI) |
|---|---|---|
| STAT3C-GFP | 1/85,840 (1/25231-1/292046) | 208 (61-709) |
| GFP | 1/279,382 (1/109,682-1/711,641) | 14 (6-36) |

CI, confidence interval.

Table 2 shows changes in CRU in primary recipients during the process of engraftment. While GFP transduced bone marrow cells produced 14 CRU in cells obtained from 2 femurs and 2 tibias, the cells transduced with STAT3-C produced about 208 CRUs in simultaneous experiments. Thus, these results show that increasing STAT3 activity in the stem cells induces enhanced self-renewal in-vivo and thereby increases net regeneration by the modified stem cells.

Example 6

Ex-Vivo Expansion of Stem Cells by Co-Culture with Cells Transduced by STAT3-C Increased STAT3 activities in stem cells leads to increased self-renewal and stem cell activities for regeneration.

Here, experiments were performed to determine whether increase in STAT3 activities can function through paracrine mechanisms, i.e. through cell-cell contact or secretion of soluble active substances.

Figure 7:
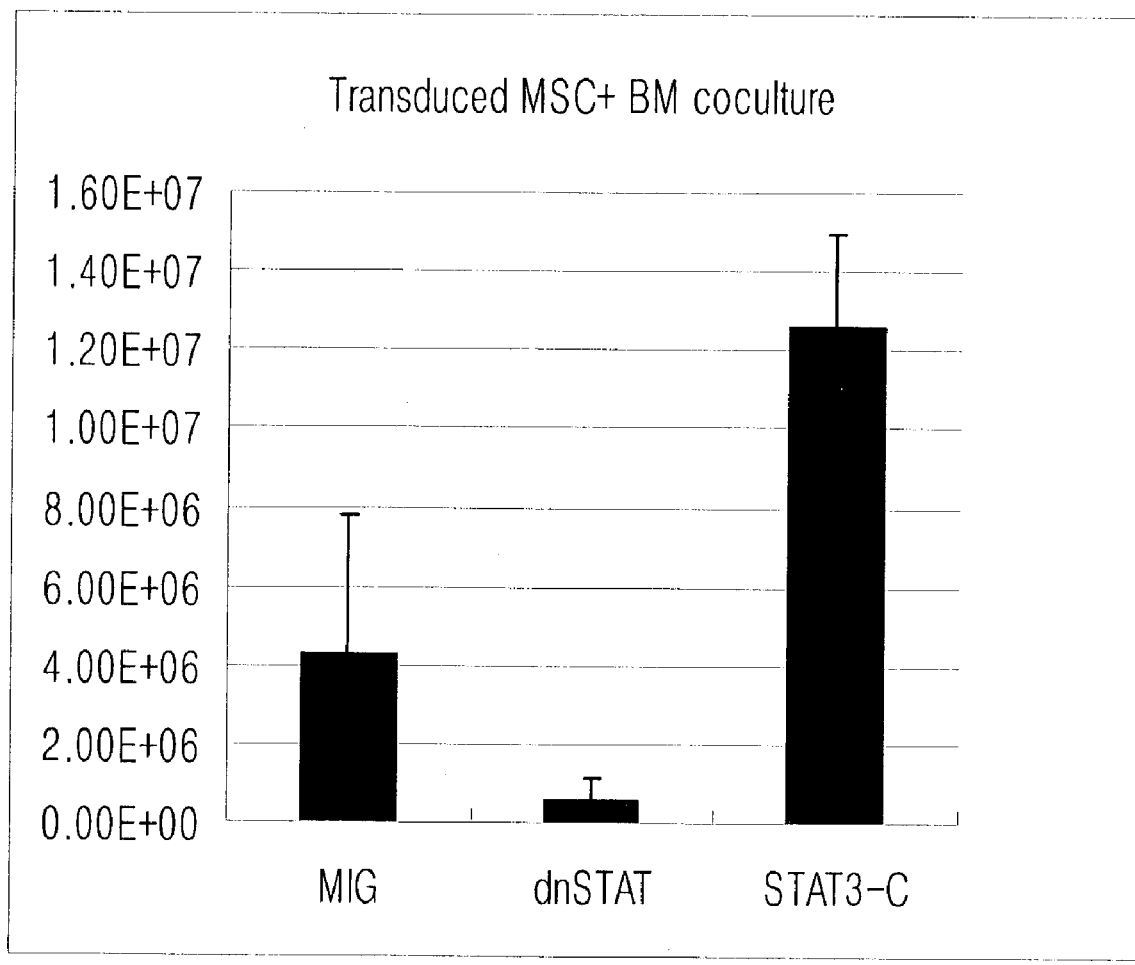
FIG. 7 shows effect of co-culturing stem cells with mesenchymal stem cells transduced with STAT3-C, dn-STAT3 or MIG vector control. Mesenchymal stem cells obtained from bone marrow were transduced with dn-STAT3, STAT3-C, or MIG. After transduction, GFP positive (transduced by each retroviral vector) was sorted and plated. Bone marrow progenitor cells obtained from 5-FU treated animal was co-cultured with these mesenchymal stem cells and the culture was continued for five days. Each group of cells was transplanted into irradiated mice and % donor cell repopulation was analyzed by FACS on donor cell specific markers (Ly5.2) 3 weeks after transplantation. As shown in the figures, mesenchymal stem cells cultured on the mesenchymal stem cells transduced with STAT3-C show marked increase in in-vivo engraftment assessed at post-transplantation 3 weeks.

To investigate this possibility, mesenchymal stem cells (MSC) were established from bone marrow and transduced with STAT3-C, dn-STAT3 and MIG. After gene transduction of each gene, GFP positive cells (transduced cells) were sorted by FACS and co-cultured with donor cells (C57BL6/Ly5.2) for five days in the presence of cytokines above mentioned. Thus, cultivated cells were transplanted into recipient mice (Pep3b/Ly5.1) and donor engraftment was analyzed. FIG. 7 shows representative data obtained from such experiments. As shown in the data, increase of STAT3 activity in the neighboring adherent MSC cells can also lead to enhancement of in-vivo regenerative activity of co-cultured stem cells. This result shows that STAT3 mediated enhancement of stem cell activity may function both through direct intracellular signaling mechanisms as well as though paracrine mechanisms.

This result also shows that under the conditions that can manipulate STAT3 activities in the feeder cells, these feeder cells can be used to enhance stem cell activities by co-culture system or by using their soluble factors secreted.

References

1. Danet G H, Lee H W, Luongo J L, Simon M C, Bonnet D A. Dissociation between stem cell phenotype and NOD/SCID repopulating activity in human peripheral blood CD34 (+) cells after ex vivo expansion. Exp Hematol. Dec.29,2001; (12):1465-73.

2. Dorrel C, Gan O I, Pereira D S, Hawley R G, Dick J E (2000), Blood, 95, 1, 102-110: Expansion of human cord blood CD34+CD38– cells in ex vivo cultue during retroviral transduction without a corresponding inrease in SCID repopulating cell SRC) frequency: dissociation of SRC phenotype and function.

3. Eglitis M A, Mezey E. Hematopoietic cells differentiate into both microglia and macroglia in the brains of adult mice. Proc Natl Acad Sci USA. Apr. 15,1997;94(8):4080-5.

4. Hanazono Y, Nagashima T, Takatoku M, Shibata H, Ageyama N, Asano T, Ueda Y, Dunbar C E, Kume A, Terao K, Hasegawa M, Ozawa K. In vivo selective expansion of gene-modified hematopoietic cells in a nonhuman primate model. Gene Ther. August 2002;9(16):1055-64.

5. Il-Hoan Oh, Eaves C J, 2000, Retrovirus mediated overexpression of a dominant negative form of STAT3 selectively impairs long term repopulating stem cell activity without affecting later stages of hematopoiesis, 2000, *Blood,* 96,11, 275

6. Lagasse E. Connors H, A1-Dhalimy M, Reitsma M, Dohse M, Osborne L, Wang X, Finegold M, Weissman I L, Grompe M. Purified hematopoietic stem cells can differentiate into hepatocytes in vivo. Nat Med. November 2000;6(11): 1229-34.

7. Larochelle A, Vormoor J, Hanenberg H, Wang J C, Bhatia M, Lapidot T, Moritz T, Murdoch B, Xiao X L, Kato I, Williams D A, Dick J E. Identification of primitive human hematopoietic cells capable of repopulating NOD/SCID mouse bone marrow: implications for gene therapy. Nat Med. December 1996;2(12):1329-37.

8. Matsuda T, Nakamura T, Nakao K, Arai T, Katsuke M, Heike T, Yokita T (1999) EMBO Journal, 18, 15, 4261-4269, STAT3 activation is sufficient to maintain an undifferentiated state of mouse embryonic stem cells.

9. Niwa H, Burdon T, Chambers I, Smith A (1998) Genes & Development, 12, 13, 2048-2060, Self-renewal of pluripotent embryonic stem cells is mediated via activation of STAT3.

10. Orlic D, Kajstura J, Chimenti S, Jakoniuk I, Anderson S M, Li B, Pickel J, McKay R, Nadal-Ginard B, Bodine D M, Leri A, Anversa P. Bone marrow cells regenerate infarcted myocardium. Nature. Apr. 5, 2001;410(6829):701-5.

11. Poulsom R, Forbes S J, Hodivala-Dilke K, Ryan E, Wyles S, Navaratnarasah S, Jeffery R, Hunt T, Alison M, Cook T, Pusey C, Wright N A. Bone marrow contributes to renal parenchymal turnover and regeneration. J Pathol. September 2001;195(2):229-35.

12. Sauvageau G, Thorsteinsdottir U, Eaves C J, Lawrence H J, Largman C, Lansdorp P M, Humphries R K. Overexpression of HOXB4 in hematopoietic cells causes the selective expansion of more primitive populations in vitro and in vivo. Genes Dev. Jul. 15, 1995;9(14):1753-65.

13. Xu R, Reems J A. Umbilical cord blood progeny cells that retain a CD34+ phenotype after ex vivo expansion have less engraftment potential than unexpanded CD34+ cells. Transfusion. February 2001; 41(2):213-8.

14. U.S. Pat. No. 6,235,873.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. An isolated mammalian hematopoietic stem cell, modified to comprise a protein comprising an activated STAT3 polypeptide fused to a protein transduction domain (PTD), wherein the activated STAT3 polypeptide fused to a PTD is a chimeric protein comprising STAT3-C and TAT, and wherein the chimeric protein further comprises six histidine residues;

wherein the cell as modified has in vitro or in vivo proliferative activity while maintaining its undifferentiated phenotype; and wherein the cell as modified is a multipotent stem cell that can differentiate into a non-hematopoietic cell as well as into a hematopoietic cell.

2. The stem cell of claim 1, which is a human stem cell.

3. The stem cell of claim 1, which is obtained from umbilical cord blood.

4. The stem cell of claim 1, wherein the activated STAT3 polypeptide fused to a PTD is delivered into the cell by protein transduction.

5. The stem cell of claim 1, wherein the cell is isolated from bone marrow.

6. The stem cell of claim 2, which is obtained from umbilical cord blood.

7. The stem cell of claim 2, wherein the activated STAT3 polypeptide fused to a PTD is delivered into the cell by protein transduction.

8. The stem cell of claim 3, wherein the activated STAT3 polypeptide fused to a PTD is delivered into the cell by protein transduction.

* * * * *